United States Patent
Anderson

(10) Patent No.: US 8,317,342 B2
(45) Date of Patent: Nov. 27, 2012

(54) SURFACE PREPARATION METHOD FOR ELIMINATING OPTICAL INTERFERENCE FROM ABSORPTION CAVITY MIRRORS

(75) Inventor: Tyler Anderson, Lincoln, NE (US)

(73) Assignee: LI-COR, Inc., Lincoln, NE (US)

( * ) Notice: Subject to any disclaimer, the term of this patent is extended or adjusted under 35 U.S.C. 154(b) by 323 days.

(21) Appl. No.: 12/572,159

(22) Filed: Oct. 1, 2009

(65) Prior Publication Data

US 2010/0091290 A1    Apr. 15, 2010

Related U.S. Application Data

(63) Continuation-in-part of application No. 12/172,103, filed on Jul. 11, 2008.

(51) Int. Cl.
*G02B 5/08* (2006.01)
(52) U.S. Cl. ..................................... 359/839
(58) Field of Classification Search .......... 359/838–884, 359/900
See application file for complete search history.

(56) References Cited

U.S. PATENT DOCUMENTS

| | | | |
|---|---|---|---|
| 2,801,570 | A | 8/1957 | Nomarski et al. |
| 2,968,220 | A | 1/1961 | Steglich |
| 4,588,267 | A | 5/1986 | Pastore |
| 7,379,224 | B2 * | 5/2008 | Tonar et al. ............ 359/265 |
| 2003/0043315 | A1 * | 3/2003 | Umemoto et al. ......... 349/65 |
| 2004/0001265 | A1 | 1/2004 | Pesik |
| 2005/0078389 | A1 * | 4/2005 | Kulas et al. ............ 359/871 |
| 2007/0029289 | A1 | 2/2007 | Brown |
| 2007/0091404 | A1 | 4/2007 | Miyamoto |
| 2007/0242720 | A1 | 10/2007 | Eckles et al. |
| 2008/0080077 | A1 | 4/2008 | Shih et al. |

FOREIGN PATENT DOCUMENTS

WO    WO 00/31569 A1    6/2000

OTHER PUBLICATIONS

EP Application No. 10 18 3698, European Search Report and Written Opinion, 9 pages.
Morris et al. "Engineered diffusers for display and illumination systems: Design, fabrication, and applications," www.RPCphotonics.com, pp. 1-11.
Agarwal, Rahul et al., "Fabrication of Integrated Vertical Mirror Surfaces and Transparent Window for Packaging MEMS Devices," *Journal of Microelectromechanical Systems*, Feb. 1, 2007, 16(1):122-129.
European Search Report and Written Opinion for EP Application No. 08160699, dated May 31, 2012, 5 pages.

(Continued)

*Primary Examiner* — Jennifer L. Doak
(74) *Attorney, Agent, or Firm* — Leydig, Voit & Mayer, LLP; Gerald T. Gray

(57) ABSTRACT

Optical mirror elements having a diffusive backing, methods for making such optical mirror elements, and devices incorporating such optical mirror elements. The optical mirror element typically includes a first, reflective surface, and a second surface having uneven or granular features, wherein light passing through the first surface is diffusely reflected by the uneven or granular features of the second surface. The optical mirror elements are particularly well suited for use in Herriott Cell arrangements in gas analyzers.

6 Claims, 6 Drawing Sheets

OTHER PUBLICATIONS

Fraunhofer IPM, "Components Multi reflection cells," Dec. 2007, located at http://www.ipm.fraunhofer.de/fhg/ipm_en/solutions_services/processmonitoring/opt_compo . . . , last accessed on Feb. 1, 2008, 1 page.

Hecht, Eugene, "Ch. 9.7 Applications of Single and Multilayer Films," *Optics*, Jan. 1, 1998, p. 418.

"Sphärische Hohlspiegel-Substrate," Product Information Sheet, Dec. 31, 2006, p. 1. Retrieved from the Internet: URL:http://www.b-halle.de/EN/Downloads/Spherical_Concave_Mirror_Substrates.pdf.

U.S. Appl. No. 12/172,103, filed Jul. 11, 2008.

U.S. Appl. No. 13/175,426, filed Jul. 1, 2011.

* cited by examiner

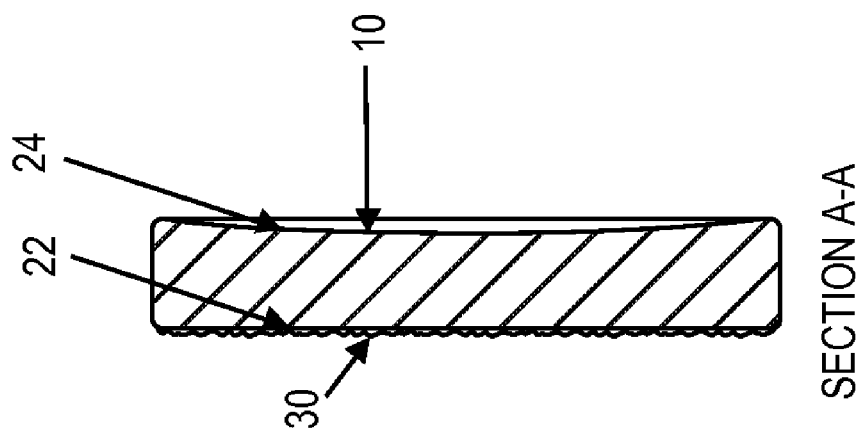
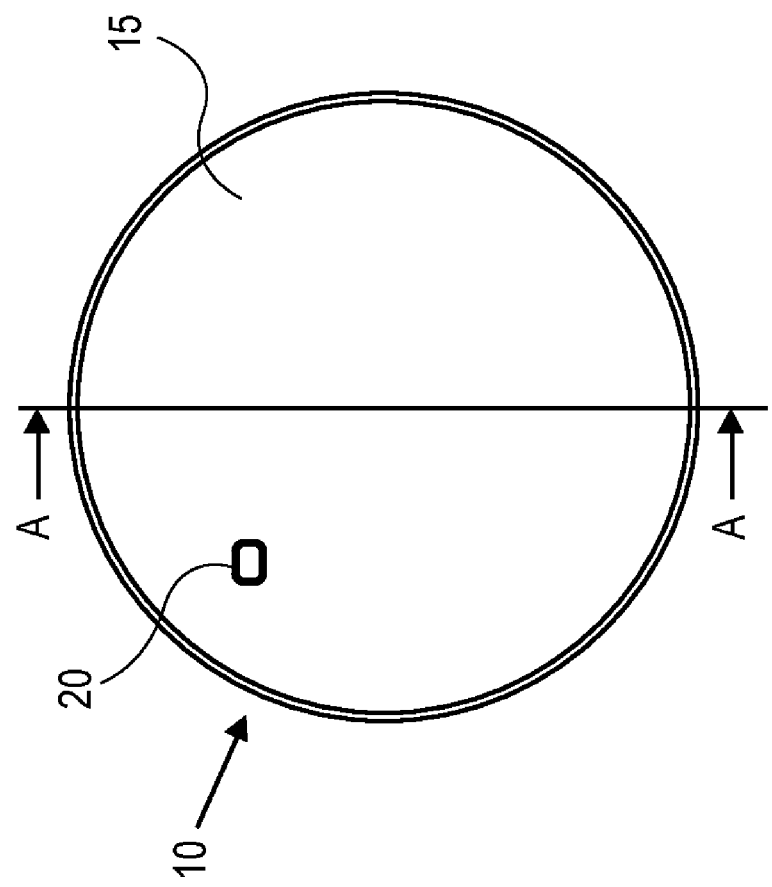

SURFACE PREPARATION METHOD FOR ELIMINATING OPTICAL INTERFERENCE FROM ABSORPTION CAVITY MIRRORS

CROSS-REFERENCES TO RELATED APPLICATIONS

The present application is a continuation-in-part of U.S. patent application Ser. No. 12/172,103, entitled PROCESS OF FORMING A LIGHT BEAM PATH IN A DIELECTRIC MIRROR, filed on Jul. 11, 2008, which is hereby incorporated by reference in its entirety for all purposes.

STATEMENT AS TO RIGHTS TO INVENTIONS MADE UNDER FEDERALLY SPONSORED RESEARCH OR DEVELOPMENT

This work was supported in part by a grant from the SBIR/DOE, DE-FG02-05ER84283. The government may have certain rights in this invention.

BACKGROUND

The present invention relates generally to optical devices, and more particularly to optical mirror elements having optically diffusive backings.

Devices such as gas analyzers typically include internal absorption cavities defined by two end mirrors. A laser beam or other light source enters the cavity and reflects back and forth between the mirror end faces to provide a long path length. A long path length allows for better absorption of the light by trace gases, and hence detection of trace gases. Path lengths of between about 1 meter and 100 meters are typical and path lengths on the order of a kilometer are possible. For a confocal cavity arrangement, such as may be found in a Herriott Cell, beam entry into the cavity is typically off axis at a certain entry point. The beam reflects off of the concave-shaped end mirrors at discrete reflection points until it exits the entry point or other defined aperture. Typically, the entry point, and other aperture(s), are formed by drilling a hole in the mirror element to allow for entry of light into the cavity.

For in-the-field applications, such as use of a portable gas analyzer to test trace gases on site, it is desirable to maintain a controlled environment within the Herriott Cell cavity. To realize such applications, the physical hole(s) are filled with a glass plug to keep the cavity environment contained and to make the device robust for field use (i.e., to prevent contaminants from entering the cavity). However, use of a glass plug can be difficult and costly, and it may introduce noise due to reflections around the perimeter of the hole. Additionally, the process of drilling and filling with a glass plug can be costly and time-consuming, and may limit the cavity sizes that can be used.

Dielectric mirrors are often used to provide low optical losses in absorption cavities. Dielectric mirrors, however, allow a small percentage of light to transmit through the reflective surface, which can then be reflected from the back surface of the substrate. Interference from this superfluous optical path can be detected as a change in intensity that may look similar to a gas absorption profile and which would degrade accuracy of absorbance measurements. Soft metal coatings may be used to reduce such interference. However, such coatings are not robust and are not well suited to field applications.

Therefore it is desirable to provide methods and devices that overcome the above and other problems. In particular, it is desirable to provide mirror elements, and methods of manufacturing the same, that overcome the above problems.

BRIEF SUMMARY

The present invention provides optical mirror elements having a diffusive backing, methods for making such optical mirror elements, and devices incorporating such optical mirror elements. The optical mirror elements are particularly well suited for use in Herriott Cell arrangements in gas analyzers.

According to one embodiment, an optical mirror element is provided that typically includes a first, reflective surface, and a second surface having uneven or granular features, wherein light passing through the first surface is diffusely reflected by the uneven or granular features of the second surface. In certain aspects, the first, reflective surface includes one or more layers of dielectric material. In certain aspects, the uneven or granular features are formed by sandblasting the second surface.

According to another embodiment, a method is provided for forming an optical mirror element having a diffuse backing. The method typically includes applying a reflective coating to a first surface of an optical element so as to define a reflective surface, and modifying a second surface of the optical element to define uneven or granular features, such that light passing though the first surface and impinging on the second surface is diffusely reflected by the uneven or granular features of the second surface. In certain aspects, modifying includes sandblasting the second surface of the optical element. In certain aspects, applying a reflective coating includes applying one or more layers of dielectric material. In certain aspects, the optical element is an optically transmissive element.

According to yet another embodiment, a method is provided for forming an optical mirror element having a diffuse backing. The method typically includes applying a reflective coating to at least a portion of a first surface of an optical element so as to define a reflective surface, and modifying at least a portion of a second surface of the optical element to define a diffuse reflector portion, such that light passing though the first surface and impinging on the second surface is diffusely reflected by the diffuse reflector portion of the second surface. In certain aspects, modifying includes sandblasting the second surface of the optical element. In certain aspects, applying a reflective coating includes applying one or more layers of dielectric material. In certain aspects, the optical element is an optically transmissive element.

According to a further embodiment, an optical cavity device is provided that typically includes a first mirror element having an internal reflective surface and an exterior surface having uneven or granular features, wherein light passing through the internal reflective surface is diffusely reflected by the uneven or granular features of the exterior surface, and a second mirror element having an internal reflective surface and an exterior surface, and a housing structure configured to hold the first and second mirrors such that the internal surfaces are facing each other along a common axis. In certain aspects, the exterior surface of the second mirror element has uneven or granular features, wherein light passing through the internal reflective surface of the second mirror element is diffusely reflected by the uneven or granular features of the exterior surface of the second mirror element. In certain aspects, the internal surfaces of both the first and second mirror elements have a concave geometry. In certain aspects, a first portion of the interior surface of the first mirror element comprises a reflective coating defining a reflective surface, and wherein a second portion of that internal surface comprises an anti-reflective coating defining an optically transmissive window in the reflective surface.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

BRIEF DESCRIPTION OF THE DRAWINGS

FIGS. 1A-1C illustrate an optical mirror element having a reflective surface, a diffusive surface (e.g., diffusive backing surface) and a window portion according to one embodiment.

DETAILED DESCRIPTION OF THE INVENTION

The present invention provides optical mirror elements having a diffusive backing surface, methods for making such optical mirror elements, and devices incorporating such optical mirror elements. The optical mirror elements are particularly well suited for use in Herriott Cell arrangements in gas analyzers.

In some embodiments, a window feature or aperture is provided to facilitate transmission of light through a portion of the optical element defined by the window feature or aperture. One skilled in the art will also understand that the optical elements need not have a window feature; however, having such a window facilitates light passing through the mirror element without interference, which can be particularly useful for various application such as introducing a light beam into a Herriot cell arrangement. Accordingly, use of and inclusion of a window feature or aperture as discussed herein is entirely optional.

Figure 1C:
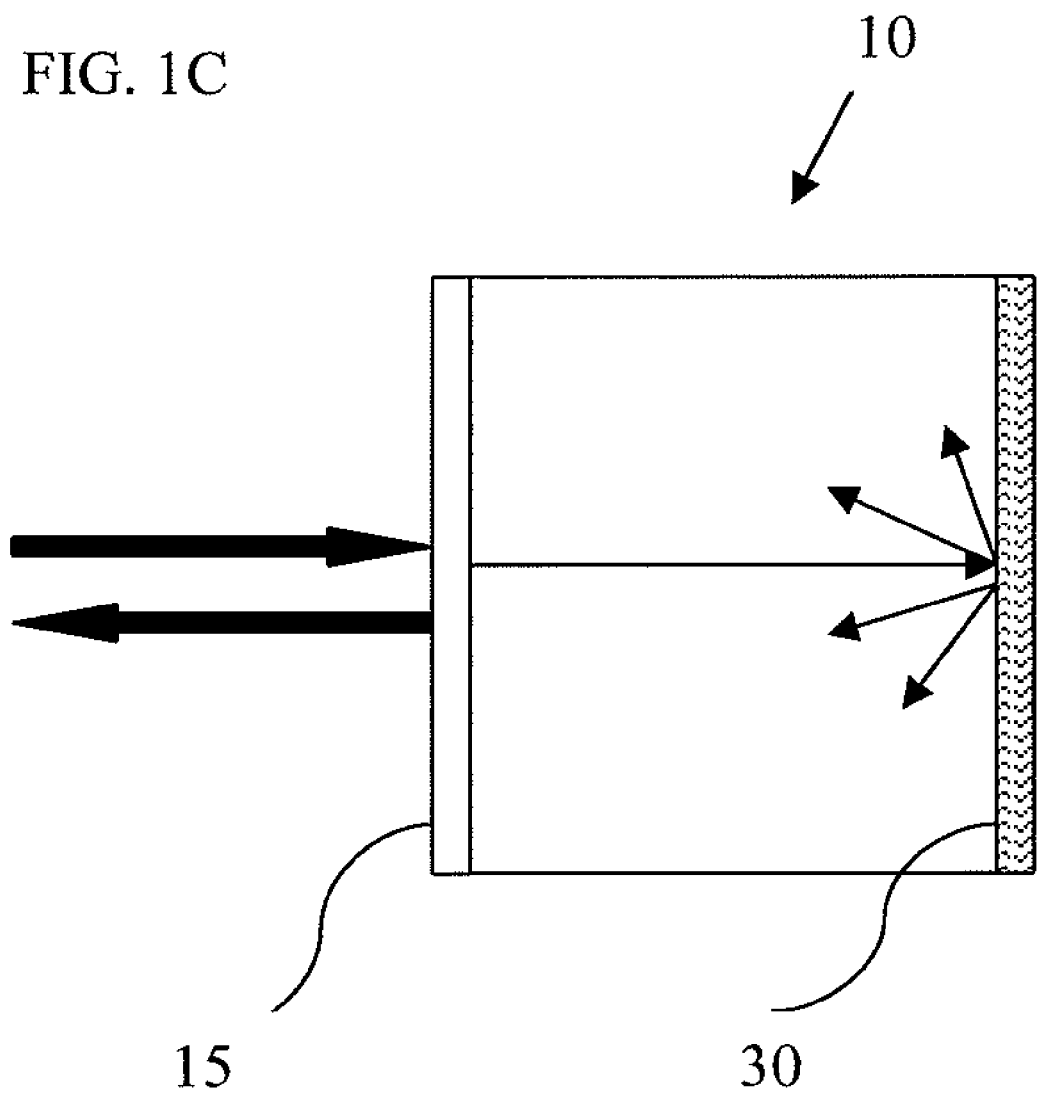

FIG. 1 illustrates an optical mirror element having a reflective surface, a diffusive surface (e.g., diffusive backing surface) and a window portion according to one embodiment. FIG. 1a shows a frontal view of the mirror surface and FIG. 1b shows a side view of the mirror element and FIG. 1c shows an expanded side view of the mirror element. As shown mirror element 10 has a reflective mirror surface 15 with a window feature or aperture 20 that allows light to pass through the mirror surface. Window 20 may take on a circular shape, a rectangular shape or any other shape as is desired, and may be located at an place on the reflective surface as desired. A diffusive backing 30 facilitates removal or reduction of interfering reflections caused by the small percentage of light that may pass through the reflective mirror surface 15. As used herein, diffusive surface refers to any surface that has diffusive optical properties such that light impinging on the diffuse surface is reflected or refracted at a number of different angles. The scatter properties of the diffusive surface may be homogenous or non-homogenous. A diffusive surface generally includes granular or uneven surface features. Hence, in certain aspects, light passing through the reflective surface is diffusely reflected by the uneven or granular features of the diffuse reflective surface.

In one embodiment, the reflective mirror surface 15 includes a reflective coating layer that defines a mirror surface. A first portion of the mirror surface does not include the reflective coating layer such that that portion defines an optically transmissive window 20 in the mirror surface. The mirror element 10 shown in FIG. 1 has a flat end face 22 on which the diffusive surface is defined, and a concave face 24 on which the mirror surface 15 is defined. One skilled in the art will recognize that the mirror element may have any other shape or configuration as desired. That is, the diffusive surface may be defined on a surface that is not flat, but which may be concave or convex or which may have any other geometry or configuration.

Figure 2:
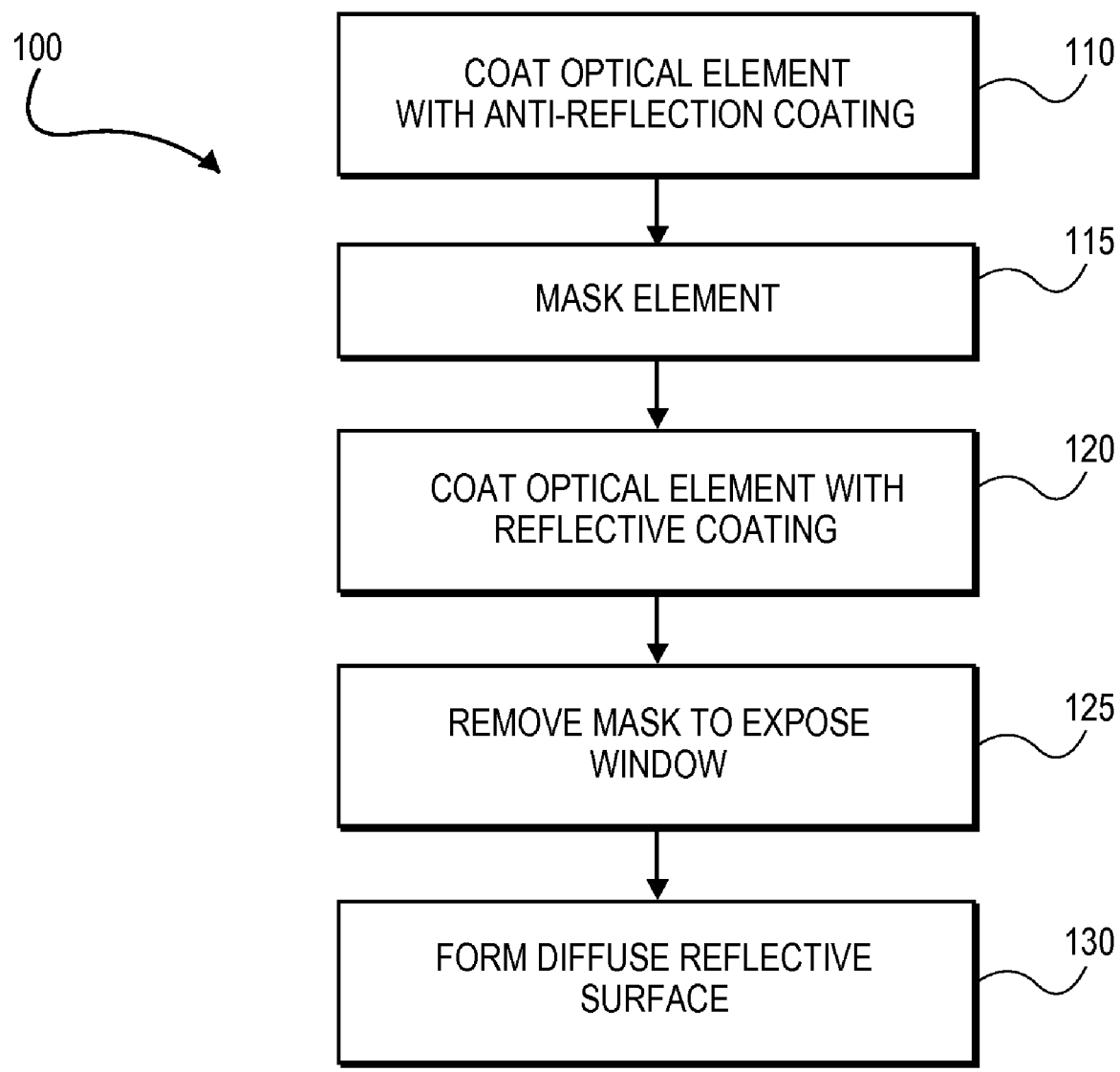
FIG. 2 illustrates a method of fabricating a mirror element 10 having a diffuse backing 30 according to one embodiment.

FIG. 2. illustrates a method 100 of fabricating a mirror element 10 having a diffuse backing 30 according to one embodiment. In step 110, a first surface of an optically transmissive element, e.g., optical flat, lens, etc, is coated with a dielectric, anti-reflective coating (e.g., thin-film coatings or interference coatings). In one aspect, a single stack dielectric coat is applied. For example, coating techniques such as chemical vapor deposition (CVD), sputtering, physical vapor deposition, physical liquid deposition, chemical liquid deposition (e.g., electroplating) and others may be used as are well known. The optically transmissive element may be made of fused silica or other optically transmissive material. Coating step 110 may include coating the optical element with one or more layers of anti-reflective material. Useful anti-reflective coating materials, according to certain aspects, include oxide layers such as silicon dioxide ($SiO_2$), $TiO_2$, $Al_2O_3$ and tantalum oxide ($Ta_2O_5$), and/or other oxides including metal oxides, with appropriate thicknesses for the wavelength range of the radiation to be used. For dielectric coatings two materials with different index of refractions are needed. Another useful anti-reflective coating is a single coating of Magnesium Fluoride (MgF).

In optional step 115, a mask is provided to cover the portion of the first surface that will define the window portion 20. The mask may be a tape or other material as is well known, or it may include a tab or other element that is positioned to cover the window portion. One useful tape that works well in vacuum conditions is Kapton® Tape. In step 120, the first surface is coated with a dielectric, reflective coating (e.g., thin-film coatings or interference coatings) to create the mirror surface. For example, coating techniques such as CVD, sputtering, physical vapor deposition, physical liquid deposition, chemical liquid deposition (e.g., electroplating) and others may be used as are well known. This coating step may include coating the optical elements with one or more layers of reflective material. Useful reflective coating materials, according to certain aspects, include oxide layers such as silicon dioxide ($SiO_2$), $TiO_2$, $Al_2O_3$ and tantalum oxide ($Ta_2O_5$), and/or other oxides including metal oxides, with appropriate thicknesses. For dielectric reflective coatings two materials with different index of refractions are needed with appropriate thicknesses for the wavelength range of the radiation to be used. Other useful reflective coating materials, according to certain aspects, include metal coatings (i.e, gold, aluminum, silver, etc.). In step 125, the mask is removed to expose the window portion 20. For example, where the mask is a tab or other physical feature, the tab may simply be removed. Where the mask includes a chemical material or layer, the mask may be chemically removed using a solvent or other technique as is well known. It should be appreciated that, in step 110, only the first portion that will define the window portion of the first surface of the optical element need be processed (e.g., the remainder of the first surface may be masked).

In step 130, the diffusive surface 30 is formed on the second surface. In step 130, the second surface, or at least a portion of the second surface, is modified to form a diffuse reflector portion. For example, the second surface is modified to define uneven or granular features on the second surface. It should be appreciated that step 130 may occur before or after steps 110 and 125. It should also be appreciated that step 130 may be performed on a pre-made optical element. In certain aspects, a diffuse surface is formed in step 130 by removing material, by adding material or by forming the substrate with the desired properties (e.g., before further processing) using one or more (e.g., a combination) of the following procedures:

1. Removal of material. For example, a diffusive surface may be defined by etching with a chemical such as hydrofluoric acid, or by fracturing the surface with a high velocity particle such as glass beads or sand (i.e., bead blasting or sand blasting), or by grinding with a rough surface such as a diamond file or grinding tools used for glass. Bead blasting and sand blasting are generally the same process, but with different media used to fracture the surface. When etching, blasting or grinding, in certain aspects, where a window feature 20 is formed or is to be formed, the surface on which the window feature 20 is to be formed may be placed on a surface, or otherwise protected or covered during step 130 to prevent damage to the window portion area.

2. Addition of material. A diffusive surface may be defined by using materials that match the index of refraction and which are added to the second surface. For example, a UV cure optical adhesive could be applied to the second surface to form a diffusing surface. As above, steps can be taken to prevent harm to a portion of the substrate where a window feature may be or has been formed.

3. Forming the substrate with the desired properties. A diffusive surface may be defined in the substrate upon substrate formation. For example, a molded optical element could have a reflective first surface and diffuse second surface that is formed through an external tool. The diffusive surface may be a surface diffuser or a volume diffuser.

In certain aspects, areas of the diffusive surface can be left polished to allow collimated light to pass through this surface without becoming diffuse, e.g., using the window/aperture forming techniques discussed above. This may present a problem of back reflections art this surface (and in the window location), but this can be eliminated in one embodiment by using AR coatings or index matching adhesives conjunction with other optical elements to control where the glass to air interface occurs.

In certain aspects, the second surface is blackened, which also absorbs and diffuses stray reflections from this surface.

It should also be appreciated that the optical element may have any shape as desired. For example, for Herriott Cell applications it is desirable that the first surface (mirror surface) of the optical element have a concave shape (e.g., has a defined curvature profile). However, it is understood that the first surface may have or include a convex shaped surface, a flat shaped surface or other shaped surface. In one aspect, the first surface defines an interior surface of a sphere, such as may be found in an integrating sphere device, for example. Where the optical element has opposite surfaces (e.g., disk or lens element), the second surface of the optical element opposite the first surface may have any shape as desired, e.g., concave, flat, convex, etc. Additionally, the optical element may be in the shape of a prism, where the first surface (mirror surface) is substantially flat, or have any other shape as is desired.

The coatings applied can of course be tailored to the specific application(s) desired. For example, when applying a reflective coating, the reflectivity can be tailored as desired. As one example, a coating that provides for greater than about 99.9% reflectivity for wavelengths between 1645 to 1655 nm may be used. Similarly, for anti-reflective coatings, the reflectivity may be tailored as desired. As one example, an anti-reflective coating that provides for less than about 0.2% reflectivity for wavelengths between 1645 to 1655 nm may be used. One skilled in the art will recognize appropriate materials and process parameters for creating tailored reflective (and anti-reflective) coatings depending on the radiation wavelengths to be used.

Figure 3A:
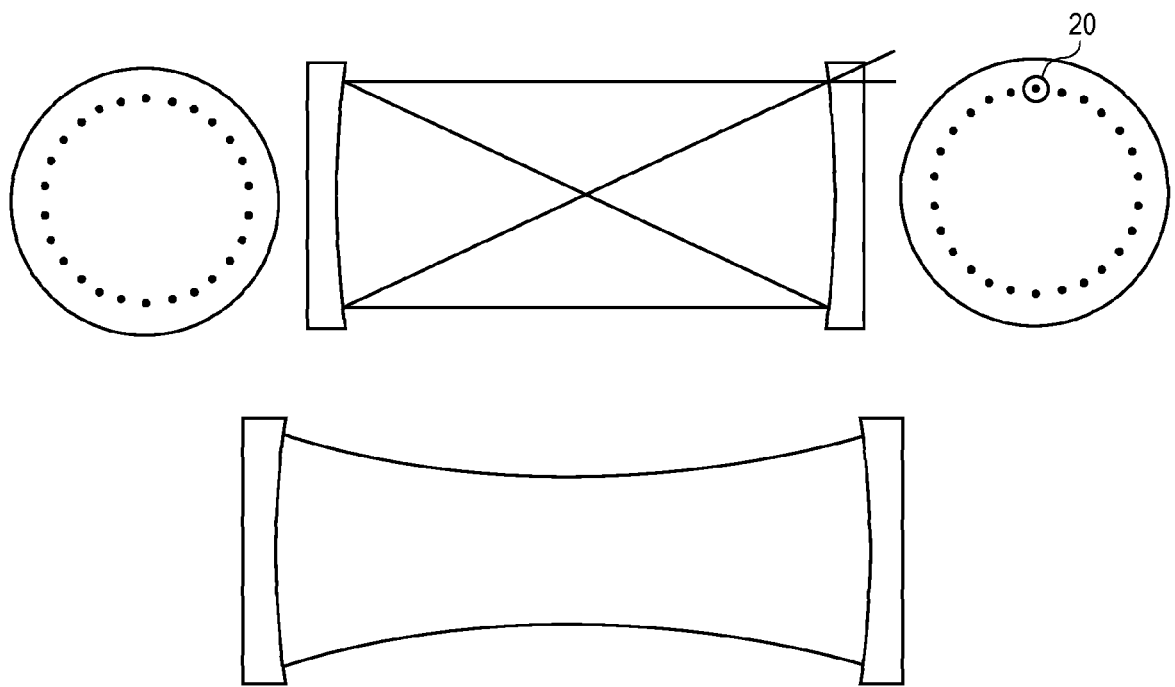
FIGS. 3A-3C illustrate examples of different arrangements of optical elements defining a cavity, such as an absorption cavity.
Figure 3B:
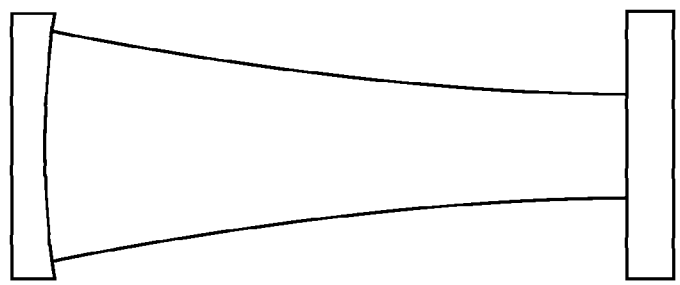
Figure 3C:
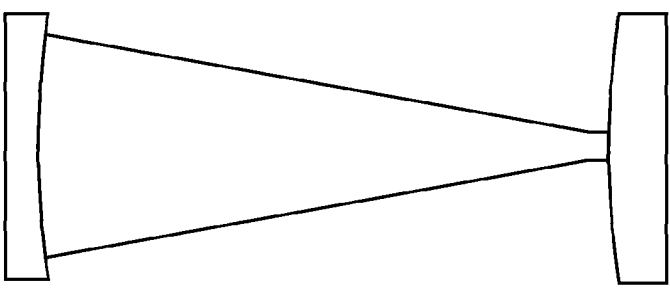

FIG. 3 illustrates examples of different arrangements of optical elements defining a cavity. As shown in FIG. 3a, a concave-concave arrangement is shown, where the beam enters the cavity through the defined window 20 and reflects off of discrete reflection points around each mirror element until the beam exits the entry point. FIG. 3b shows a concave-Plano arrangement and FIG. 3c shows a concave-convex arrangement.

Figure 4:
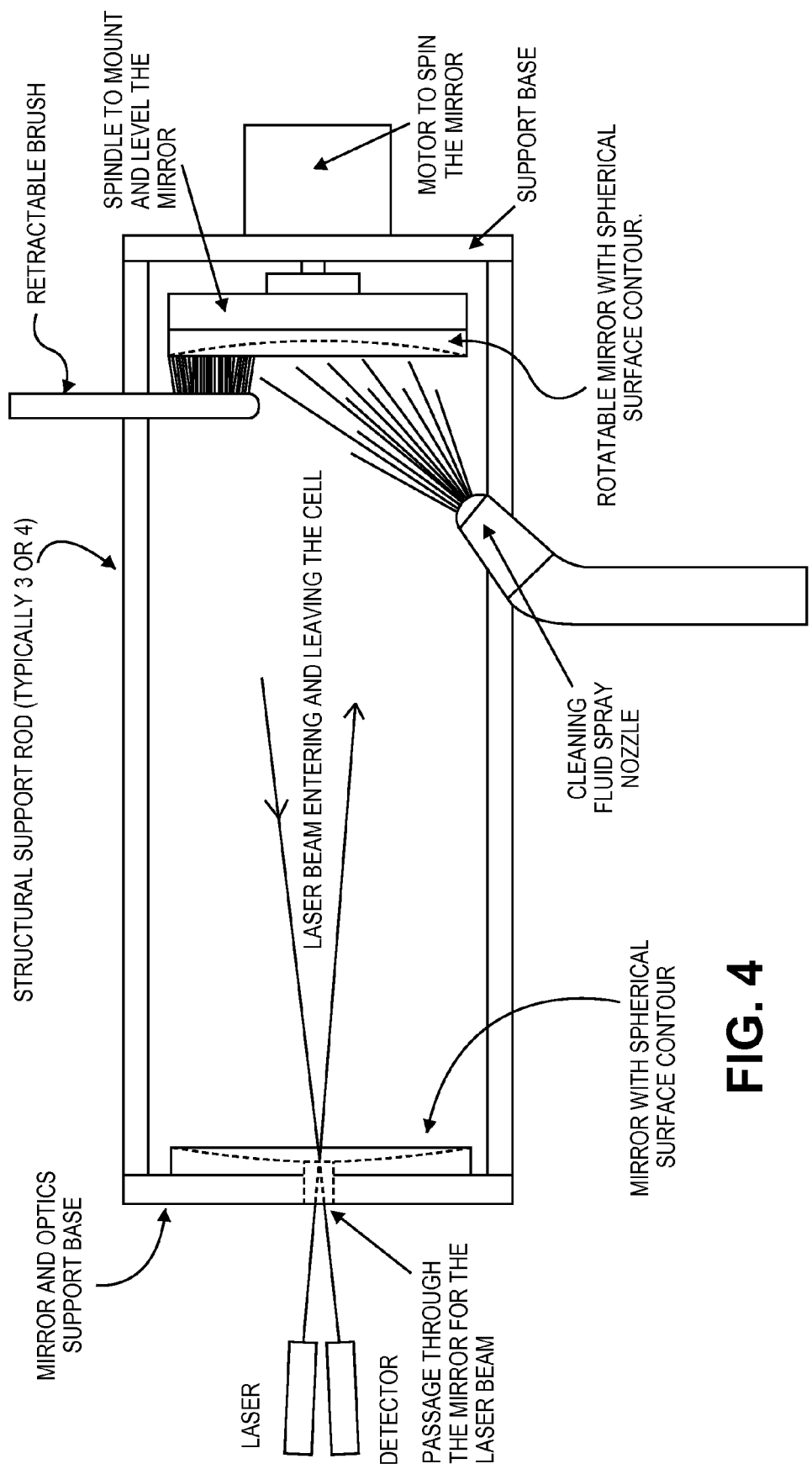
FIGS. 4 and 5 illustrate two Herriott Cell embodiments where mirror elements of the present invention are particularly useful.
Figure 5:
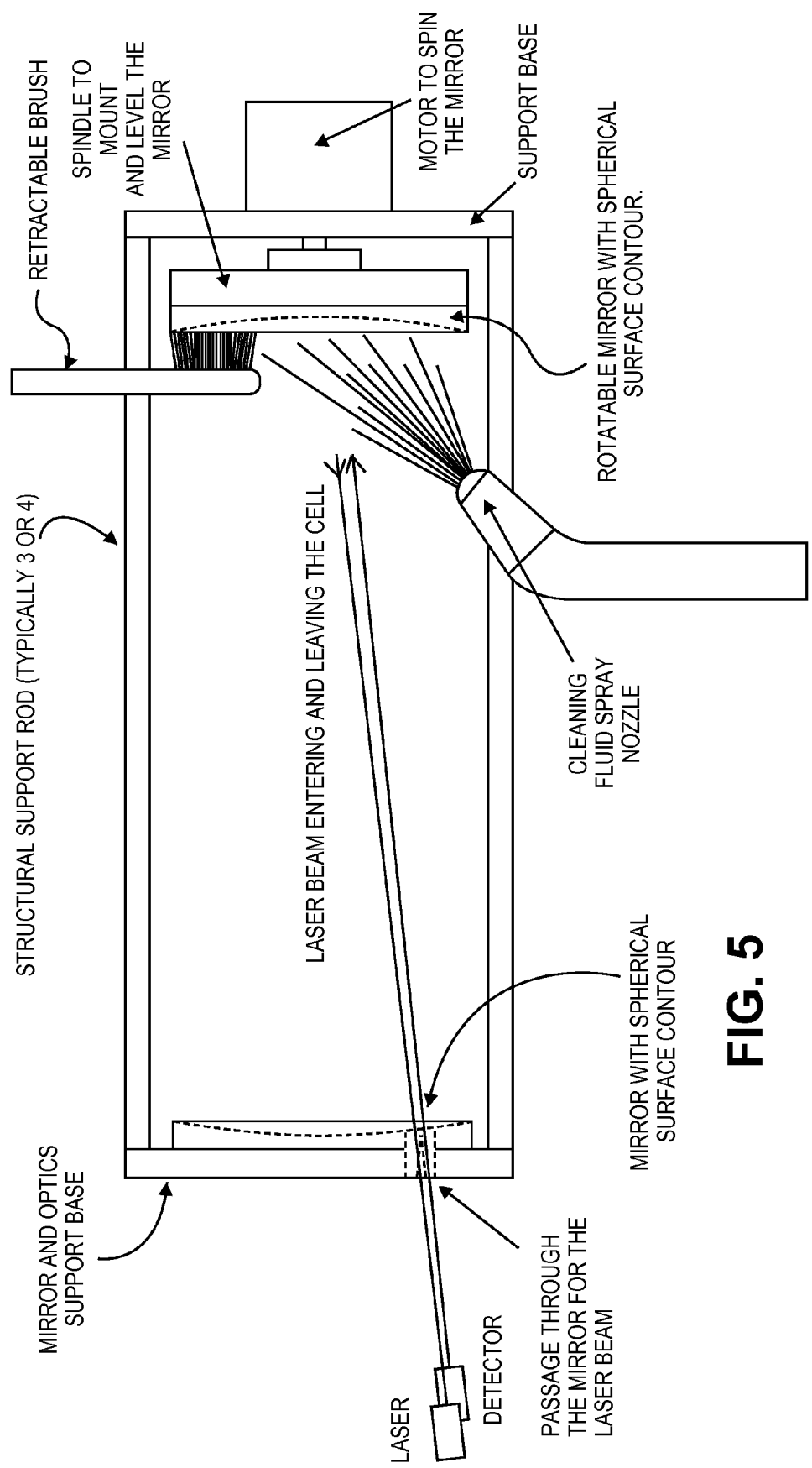

FIGS. 4 and 5 illustrate two Herriott Cell embodiments where mirror elements of the present invention are particularly useful. In the Herriott Cell arrangement of FIG. 4, the mirror element includes an entry aperture (e.g., window 20) defined in the center of the mirror element, along the axis of the device. The opposite mirror element rotates around the axis. An alternate fluid cleaning nozzle and brush are used to facilitate cleaning of the opposite mirror element. In FIG. 5, the entry aperture (e.g., window 20) is defined toward the periphery of the lens element as in FIG. 3a.

FIG. 6a shows scans of a waveform from WMS measurements with etalons present due to reflections from the back surface of a mirror element; FIG. 6b shows scans of a waveform from WMS measurements using a mirror element having a diffusive backing surface according to one embodiment. The scans are not provided for quantitative comparison, but rather qualitative comparison, as the concentrations of methane gas were different in the tests. The image in FIG. 6a shows striations through the data set, which is an etalon that is superimposed on the waveform; they do not appear as horizontal lines because in each test the temperature was changed, which causes the striations to propagate vertically through the data. Using a ground back surface on the mirror element attenuates the etalons that have a similar frequency line as the absorption line as shown in FIG. 6b. Such a mirror element structure as described herein advantageously removes areas of optical interference, which increases measurement accuracy in absorption measurements.

It should be appreciated that, as used herein, first surface does not necessarily mean the first surface that a ray of light encounters when interacting with an optical element; rather it refers to the surface that is being processed with reflective and/or anti-reflective coatings to form a mirror surface as discussed herein.

While the invention has been described by way of example and in terms of the specific embodiments, it is to be understood that the invention is not limited to the disclosed embodiments. To the contrary, it is intended to cover various modifications and similar arrangements as would be apparent to those skilled in the art. Embodiments can be used for a variety of optical devices including an integrating sphere, a Herriott cell, a White cell, a ring down cavity, an astigmatic Herriott cell, and other devices. Therefore, the scope of the appended claims should be accorded the broadest interpretation so as to encompass all such modifications and similar arrangements.

What is claimed is:

1. An optical mirror element integrated in a gas analyzer, the optical mirror element comprising:
    a first, reflective surface that reflects a substantial portion of light in a specific wavelength range impinging thereon; and
    a second surface, opposite the first surface, having a first portion with uneven or granular features, wherein any light in said specific wavelength range passing through the first surface and impinging on the first portion of the second surface is diffusely reflected by the uneven or granular features of the first portion of the second surface, wherein the optical mirror element is integrated in a gas analyzer.

2. The optical mirror element of claim 1, wherein the first, reflective surface includes one or more layers of dielectric material.

3. The optical element of claim 1, wherein the uneven or granular features are formed by sandblasting the second surface.

4. The optical element of claim 1, wherein the uneven or granular features are formed by removing material from the second surface.

5. The optical element of claim 1, wherein the uneven or granular features are formed by adding material to the second surface.

6. The optical mirror element of claim 1, wherein the second surface includes a second portion that defines an optically transmissive window portion, wherein any light in said specific wavelength range passing through the first surface and impinging on the window portion of the second surface passes through said window portion.

* * * * *